(12) United States Patent  (10) Patent No.: US 8,440,824 B2
Murai et al.  (45) Date of Patent: May 14, 2013

(54) METHOD FOR PRODUCING PYRIMIDINE COMPOUND

(75) Inventors: Shigeo Murai, Kusatsu (JP); Ryoji Koto, Yokkaichi (JP); Hiroshi Yoshizawa, Osaka (JP); Takeshi Ohshima, Kusatsu (JP); Katsuyoshi Murakami, Yokkaichi (JP); Takao Awazu, Kusatsu (JP); Hisayoshi Jonishi, Yokkaichi (JP); Takayoshi Ando, Yokkaichi (JP); Tadashi Nakamura, Yokkaichi (JP); Norio Adachi, Kusatsu (JP); Akihiko Isogai, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 125 days.

(21) Appl. No.: 12/933,980

(22) PCT Filed: Apr. 16, 2009

(86) PCT No.: PCT/JP2009/057674
§ 371 (c)(1),
(2), (4) Date: Sep. 22, 2010

(87) PCT Pub. No.: WO2009/128512
PCT Pub. Date: Oct. 22, 2009

(65) Prior Publication Data
US 2011/0021774 A1    Jan. 27, 2011

(30) Foreign Application Priority Data

Apr. 18, 2008 (JP) ................................ 2008-108898

(51) Int. Cl.
*C07D 239/02* (2006.01)

(52) U.S. Cl.
USPC .......................................... 544/330; 544/332

(58) Field of Classification Search .................. 544/312, 544/332, 330
See application file for complete search history.

(56) References Cited

U.S. PATENT DOCUMENTS

| | | | |
|---|---|---|---|
| 4,227,007 A | 10/1980 | Schirmer et al. | |
| 4,456,469 A | 6/1984 | Adams, Jr. | |
| 4,547,509 A | 10/1985 | Musser et al. | |
| 4,605,432 A | 8/1986 | Adams, Jr. | |
| 4,645,531 A | 2/1987 | Levitt | |
| 4,835,282 A * | 5/1989 | Kimura et al. | 548/213 |
| 4,935,529 A * | 6/1990 | Gerwick | 549/401 |
| 5,017,212 A | 5/1991 | Ishida et al. | |
| 5,494,886 A | 2/1996 | Kehne et al. | |
| 6,365,739 B1 | 4/2002 | Ford et al. | |
| 2004/0102636 A1 | 5/2004 | Miller et al. | |
| 2008/0200475 A1 | 8/2008 | Ennis et al. | |

FOREIGN PATENT DOCUMENTS

| | | |
|---|---|---|
| EP | 0 184 385 A2 | 6/1986 |
| EP | 0 232 067 A2 | 8/1987 |
| JP | 53 95941 | 8/1978 |
| JP | 56 139466 | 10/1981 |
| JP | 61 72756 | 4/1986 |
| JP | 64 38091 | 2/1989 |
| JP | 2002 521372 | 7/2002 |
| WO | 2006 103555 | 10/2006 |

OTHER PUBLICATIONS

J. Nowick et al., 57 Journal of Organic Chemistry 7364-7366 (1992).*
J. March, Advanced Organic Chemistry Reactions, Mechanisms and Structure 248-272 (4th ed., 1992).*
J.H. Poupaert, Drug Design: Basic Principles and Applications, in 2 Encyclopedia of Pharmaceutical Technology 1362-1369, 1367 (James Swarbrick ed., 3rd ed., 2007).*
Extended European Search Report issued Jul. 22, 2011, in Patent Application No. 09732378.6.

(Continued)

*Primary Examiner* — James O Wilson
*Assistant Examiner* — Alexander R Pagano
(74) *Attorney, Agent, or Firm* — Oblon, Spivak, McClelland, Maier & Neustadt, L.L.P.

(57) ABSTRACT

To provide a method for producing pyrimidine compound useful as an intermediate for agricultural chemicals or pharmaceuticals, which is simple in operation, presents high yield and produces only a small amount of by-products.

The method comprises reacting a compound represented by the formula (I) with a compound represented by the formula (II) in the presence of a pyridine compound to produce a compound represented by the formula (III), a compound represented by the formula (IV) or their mixture.

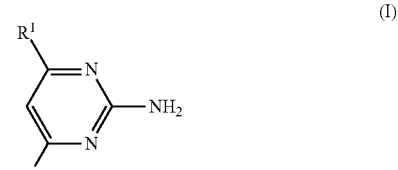

(I)

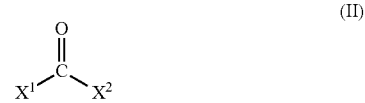

(II)

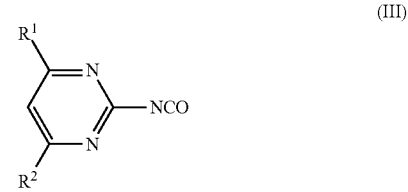

(III)

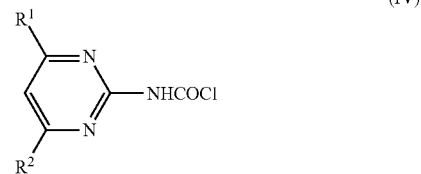

(IV)

10 Claims, No Drawings

OTHER PUBLICATIONS

James S. Nowick, et al., "An Improved Method for the Synthesis of Enantiomerically Pure Amino Acid Ester Isocyanates", The Journal of Organic Chemistry, vol. 57, No. 26, XP55002227, Dec. 1, 1992, pp. 7364-7366.

Extended European Search Report issued Apr. 12, 2012, in European Patent Application No. 12000829.7.

M. J. Gil, et al., "Synthesis and Cytotoxic Activity of N-(2-Pyridylsulfenyl) Urea Derivatives. A New Class of Potential Antineoplastic Agents.", Bioorganic & Medicinal Chemistry Letters, vol. 9, No. 16, XP-004174183, Aug. 16, 1999, pp. 2321-2324.

* cited by examiner

METHOD FOR PRODUCING PYRIMIDINE COMPOUND

TECHNICAL FIELD

The present invention relates to a method for producing a pyrimidine compound useful as an intermediate compound for an active ingredient for agricultural chemicals, pharmaceuticals, etc.

BACKGROUND ART

Each of Patent Documents 1 and 2 discloses a herbicide containing a pyridine sulfonamide compound. Examples in each document disclose a method for producing a pyrimidine compound as an intermediate compound for its production, but there is no disclosure about a method which is carried out in the presence of a pyridine compound.

PRIOR ART DOCUMENTS

Patent Documents

Patent Document 1: EP0232067A2
Patent Document 2: EP0184385A1

DISCLOSURE OF THE INVENTION

Problems to be Solved by the Invention

The method for producing a pyrimidine compound disclosed in the above Patent Documents may not necessarily be industrially satisfactory, since the operation tends to be cumbersome, the yield tends to be low, or by-products are likely to be formed.

It is an object of the present invention to provide a method for producing a pyrimidine compound, which is simple in operation, presents high yield and produces only a small amount of by-products and which is industrially useful.

Means to Solve the Problems

With respect to a method for producing a pyrimidine compound, the present inventors have found a method which is simple in operation, presents high yield and produces only a small amount of by-products.

That is, the present invention provides (1) a method which comprises reacting a compound represented by the formula (I):

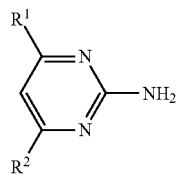

(I)

(wherein each of $R^1$ and $R^2$ is methyl, methoxy or ethoxy, and $R^1$ and $R^2$ may be the same or different from each other) with a compound represented by the formula (II):

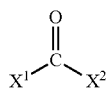

(II)

(wherein each of $X^1$ and $X^2$ is a chlorine atom or $-OCCl_3$, and $X^1$ and $X^2$ may be the same or different from each other) in the presence of a pyridine compound, to produce a compound represented by the formula (III):

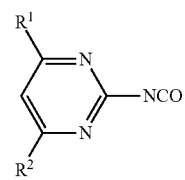

(III)

(wherein $R^1$ and $R^2$ are as defined above), a compound represented by the formula (IV):

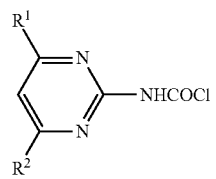

(IV)

(wherein $R^1$ and $R^2$ are as defined above), or their mixture.

Further, the present invention provides (2) a method which comprises reacting the compound of the formula (III), the compound of the formula (IV) or their mixture produced by the method as defined in the above (1), with a compound represented by the formula (V):

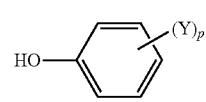

(V)

(wherein Y is alkyl, arylalkyl or halogen, and p is an integer of from 0 to 3, provided that when p is at least 2, the plurality of Y may be the same or different from one another), to produce a compound represented by the formula (VI):

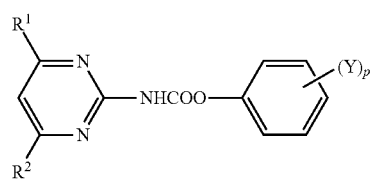

(VI)

(wherein $R^1$, $R^2$, Y and p are as defined above).

Further, the present invention provides (3) a method which comprises reacting the compound of the formula (III), the compound of the formula (IV) or their mixture produced by the method as defined in the above (1), with a compound represented by the formula (VII):

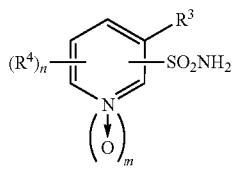

(wherein $R^3$ is —$CF_3$ or —$CON(R^5)R^6$, $R^4$ is halogen, alkyl, haloalkyl, alkoxy, haloalkoxy, alkylthio, haloalkylthio, alkoxyalkyl, haloalkoxyalkyl or —$N(R^7)R^8$, each of $R^5$ and $R^6$ is a hydrogen atom, alkyl, haloalkyl, alkenyl, alkynyl, alkoxy, haloalkoxy, alkoxyalkyl, haloalkoxyalkyl, cycloalkyl, halocycloalkyl, alkoxycarbonyl, haloalkoxycarbonyl, phenyl or halophenyl, provided that when either $R^5$ or $R^6$ is a hydrogen atom, the other is other than a hydrogen atom, $R^5$ and $R^6$ may form a heterocyclic ring together with the adjacent nitrogen atom, and $R^5$ and $R^6$ may be the same or different from each other, each of $R^7$ and $R^8$ is a hydrogen atom or alkyl, and $R^7$ and $R^8$ may be the same or different from each other, n is an integer of from 0 to 2, provided that when n is 2, two $R^4$ may be the same or different from each other, and m is 0 or 1), to produce a compound represented by the formula (VIII):

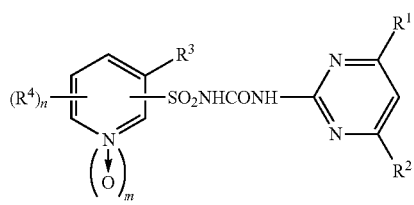

(wherein $R^1$, $R^2$, $R^3$, $R^4$, n and m are as defined above).

Further, the present invention provides (4) a method which comprises reacting the compound of the formula (III), the compound of the formula (IV) or their mixture produced by the method as defined in the above (1), with a compound represented by the formula (V):

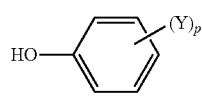

(wherein Y and p are as defined above), to produce a compound represented by the formula (VI):

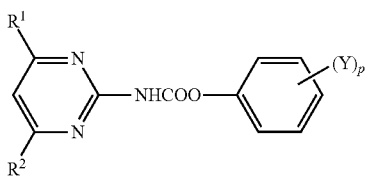

(wherein $R^1$, $R^2$, Y and p are as defined above), and further reacting the compound of the formula (VI) with a compound represented by the formula (VII):

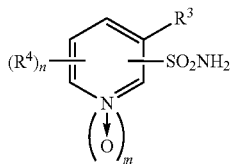

(wherein $R^3$, $R^4$, n and m are as defined above), to produce a compound represented by the formula (VIII):

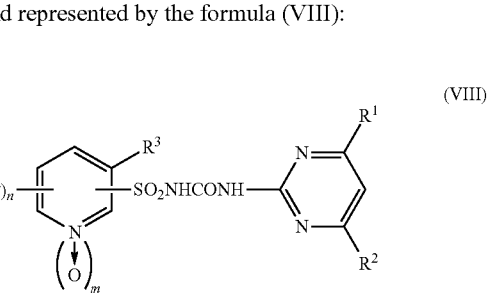

(wherein $R^1$, $R^2$, $R^3$, $R^4$, n and m are as defined above).

Further, the present invention provides (5) a method which comprises reacting the compound of the formula (VI):

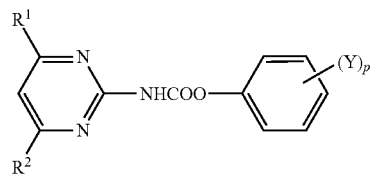

(wherein $R^1$, $R^2$, Y and p are as defined above), with a compound represented by the formula (VII):

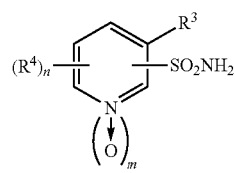

(wherein $R^3$, $R^4$, n and m are as defined above), to produce a compound represented by the formula (VIII):

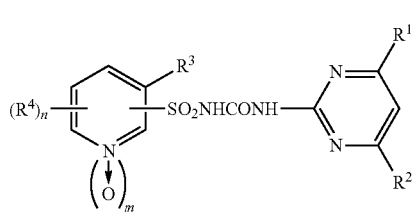

(wherein $R^1$, $R^2$, $R^3$, $R^4$, n and m are as defined above).

Advantageous Effects of the Invention

By the present invention, it is possible to produce the compound of the above formula (III) or (IV) by a method which is simple in operation, presents high yield and produced only a small amount of by-products. Further, by the present invention, it is possible to produce the compound of the above formula (III) or (IV) and then continuously produce a compound of the formula (VIII) useful as an active ingredient for agricultural chemicals by a method which is simple in operation, presents high yield and produces only a small amount of by-products.

MODE FOR CARRYING OUT THE INVENTION

Now, the production methods of the present invention will be described in detail.

Production Method (1)

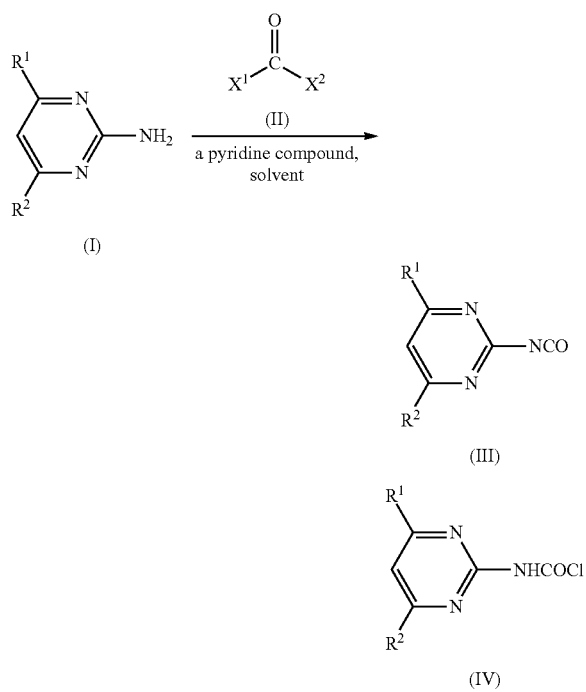

In the above formulae, $R^1$, $R^2$, $X^1$ and $X^2$ are as defined above.

In the production method (1), specific examples of the compound of the formula (II) include carbonyl chloride (phosgene), trichloromethyl chloroformate (diphosgene), bis(trichloromethyl) carbonate (triphosgene), etc. Among them, preferred is carbonyl chloride (phosgene).

In the production method (1), the amount of the compound of the formula (II) to be used, cannot generally be defined due to differences in the raw materials, the type of the solvent or the reaction conditions, but usually, based on 1 equivalent of the compound of the formula (I), the compound of the formula (II) is from 1.0 to 3.0 equivalents, preferably from 1.25 to 1.75 equivalents. Here, 1 equivalent of the compound of the formula (II) corresponds to 1 mol in the case of carbonyl chloride, 0.5 mol in the case of trichloromethyl chloroformate, or ⅓ mol in the case of bis(trichloromethyl) carbonate, to 1 mol of the compound of the formula (I).

In the production method (1), the compound of the formula (I) and the compound of the formula (II) may be added and mixed in an optional order. For example, a solution of the compound of the formula (II) may be preliminarily prepared, and the compound of the formula (I) may be added thereto, or a solution of the compound of the formula (I) may preliminarily be prepared, and the compound of the formula (II) may be added thereto. Preferably, a solution of the compound of the formula (II) is preliminarily prepared, and the compound of the formula (I) is added thereto.

The production method (1) can be carried out in the presence of a solvent. The solvent may be any solvent so long as it is inert to the reaction. It may, for example, be a halogenated hydrocarbon such as chloroform, 1,2-dichloroethane or 1,1,2-trichloroethane; an aromatic hydrocarbon such as benzene, toluene, xylene, nitrobenzene or chlorobenzene; an ester such as methyl acetate, ethyl acetate or propyl acetate; an ether such as diethyl ether, 1,4-dioxane, tetrahydrofuran (THF) or 1,2-dimethoxyethane; or a nitrogen-containing aromatic compound such as pyridine or quinoline. As the solvent, one or more of them may be optionally selected for use. Among these solvents, preferred may, for example, be a halogenated hydrocarbon or an aromatic hydrocarbon, and more preferred may, for example, be methylene chloride, 1,2-dichloroethane or chlorobenzene.

The amount of the solvent to be used cannot generally be defined due to differences in the raw materials, the type of the solvent or the reaction conditions, but usually, the solvent is from 3 to 30 parts by weight, preferably from 10 to 25 parts by weight, per 1 part by weight of the compound of the formula (I).

The production method (1) can be carried out in the presence of a pyridine compound. The pyridine compound cannot be generally defined due to differences in the raw materials, the type of the solvent or the reaction conditions, but it may, for example, be pyridine substituted by alkyl, pyridine substituted by amino, pyridine substituted by alkylamino, pyridine substituted by alkyl and amino, or pyridine. In a case where a pyridine compound having substituents is to be used, the number of substituents in the pyridine compound may be from 1 to 5, and the position of such a substituent may be at any of from 2- to 6-positions of pyridine. As the pyridine compound, one or more of them may suitably be selected for use. Among such pyridine compounds, preferred may, for example, be an alkyl substituted pyridine, or pyridine, and more preferred may, for example, be methyl- or ethyl-substituted pyridine, or pyridine. Further preferred may, for example, be 3-methylpyridine, 2,6-dimethylpyridine, or pyridine, and still further preferred may, for example, be 3-methylpyridine, or pyridine.

The amount of the pyridine compound to be used cannot generally be defined due to differences in the raw materials, the type of the solvent or the reaction conditions, or since the compound of the formula (III), the compound of the formula (IV) or their mixture obtained by the production method (1) may sometimes be used continuously in the following production method (2), (3) or (4) without purification, but usually, the pyridine compound is from 0.05 to 3.0 mol, preferably from 0.075 to 2.75 mol, to 1 mol of the compound of the formula (I).

Here, the pyridine compound may be added and mixed in an optional order. For example, it may be added before or after the addition of the compound of the formula (I), the compound of the formula (II) and the solvent, or it may be added simultaneously with any one of them or all of them. Preferably, the pyridine compound may be added after mixing the compound of the formula (I) and the compound of the formula (II).

The production method (1) may be carried out in the presence of a basic compound, as the case requires. In such a case, there may be a case where preferred results can be obtained such that the yield is improved, and formation of by-products can be suppressed. The basic compound may, for example, be a chain or cyclic aliphatic amine such as triethylamine, tri-n-propylamine, triisopropylamine, tri-n-butylamine, tri-secondary butylamine, triisobutylamine, tri-tertiary butylamine, diethylisopropylamine, N-methylpiperidine, N-ethylpiperidine or N-methylpyrrolidine; an aromatic amine such as N,N-dimethylaniline; an alkali metal carbonate such as sodium carbonate or potassium carbonate; an alkali metal hydrogencarbonate such as sodium hydrogencarbonate or potassium hydrogencarbonate; an alkaline earth metal carbonate such as barium carbonate or calcium carbonate; an alkali metal hydroxide such as sodium hydroxide or potassium hydroxide; 1,8-diazabicyclo[5.4.0]-7-undecene (DBU); 1,5-diazabicyclo[4.3.0]-5-nonene (DBN); or quinoline. As the basic compound, one or more of them may suitably be selected for use. Among them, a preferred basic compound may, for example, be a chain or cyclic aliphatic amine. More preferred may, for example, be triethylamine.

The amount of the basic compound to be used cannot generally be defined due to differences in the raw materials, the type of the solvent or the reaction conditions, or since the compound of the formula (III), the compound of the formula (IV) or their mixture obtained by the production method (1) may sometimes be used continuously in the following production method (2), (3) or (4) without purification, but usually the basic compound is from 0.1 to 7.0 equivalents, preferably from 2.0 to 5.5 equivalents, to 1 equivalent of the compound of the formula (I). Here, 1 equivalent of the basic compound corresponds to 1 mol in the case of a monovalent basic compound such as triethylamine, or corresponds to 0.5 mol in the case of a bivalent basic compound such as sodium carbonate.

Further, the basic compound may be added and mixed in an optional order. For example, it may be added before or after the addition of the compound of the formula (I), the compound of the formula (II), the solvent and the pyridine compound, or it may be added simultaneously with any one of them or all of them. Preferably, the basic compound may be added simultaneously with the pyridine compound.

The reaction temperature for the production method (1) cannot generally be defined due to differences in the raw materials, the type of the solvent or the reaction conditions, and heating or cooling may optionally be carried out. Usually, the reaction can be carried out within a range of from 0 to 50° C., preferably from 10 to 40° C.

The reaction time for the production method (1) cannot generally be defined due to differences in the raw materials, the type of the solvent or the reaction conditions, but usually, it is from one minute to 24 hours, preferably from one minute to 3 hours.

Formation of the compound of the formula (III) or (IV) in the production method (1) can be confirmed, for example, in such a manner that a portion of the reaction mixture is sampled, and the compound of the formula (III) or (IV) as the reaction product is reacted with an alcohol such as methanol, ethanol or propanol to obtain an alkyl carbamate represented by the formula (a):

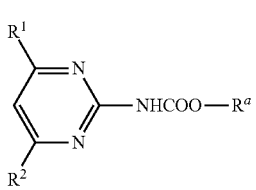

(a)

(wherein $R^1$ and $R^2$ are as defined above, and $R^a$ is alkyl), which is detected by liquid chromatography. Specifically, it can be confirmed by a peak ratio between the compound of the formula (I) as the raw material and the above alkyl carbamate.

Production Method (2)

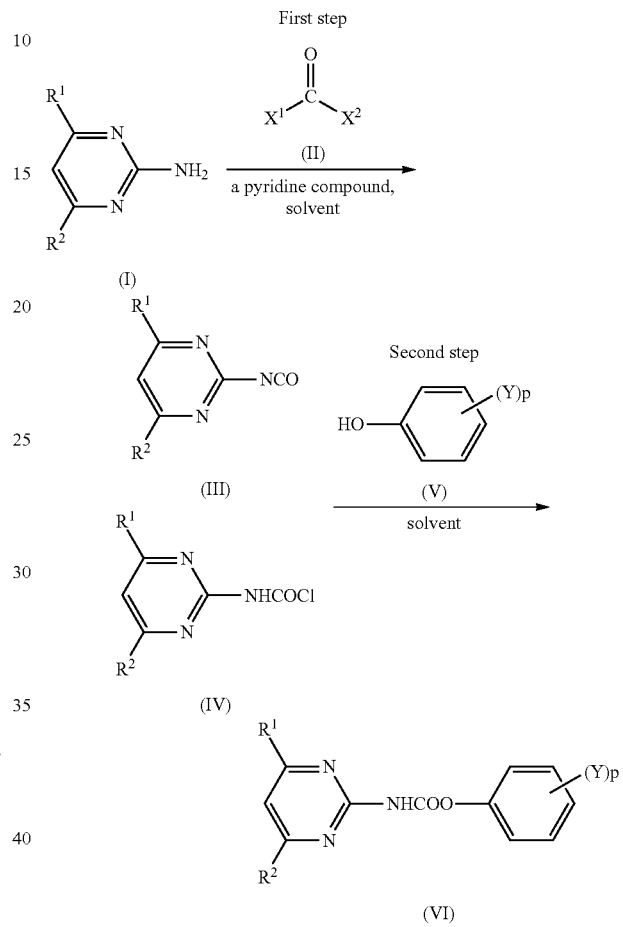

In the above formulae, $R^1$, $R^2$, $X^1$, $X^2$, Y and p are as defined above.

Specific examples of Y include methyl, ethyl, n-propyl, isopropyl, n-butyl, secondary butyl, tertiary butyl, benzyl, a chlorine atom, etc.

The first step of the production method (2) is carried out in accordance with the above-described production method (1).

In the second step of the production method (2), the amount of the compound of the formula (V) cannot generally be defined due to differences in the raw materials, the type of the solvent or the reaction conditions, but usually, the compound of the formula (V) is from 1.0 to 3.0 mol, preferably from 1.0 to 1.75 mol, to 1 mol of the compound of the formula (I).

In the second step of the production method (2), the compound of the formula (III) or (IV) and the compound of the formula (V) may be added and mixed in an optional order. For example, a mixture of the compound of the formula (V) and the solvent is preliminarily prepared, and the reaction mixture obtained in the first step may be added thereto without purification, or to the reaction mixture obtained in the first step, the compound of the formula (V) may be added as it is, or after preliminarily preparing a mixture of the compound of the formula (V) and the solvent. Preferably, to the reaction mixture obtained in the first step, the compound of the formula (V) may be added without being mixed with a solvent.

The second step of the production method (2) can be carried out in the presence of a solvent. The solvent may be any solvent so long as it is inert to the reaction. For example, ones exemplified in the above production method (1) may be mentioned. One or more of them may suitably be selected for use as the solvent. Among these solvents, preferred may, for example, be a halogenated hydrocarbon or an aromatic hydrocarbon, and more preferred may be methylene chloride, 1,2-dichloroethane or chlorobenzene.

The amount of the solvent cannot generally be defined due to differences in the raw materials, the type of the solvent or the reaction conditions, but usually, the solvent is from 3 to 30 parts by weight, preferably from 10 to 25 parts by weight, to 1 part by weight of the compound of the formula (I).

The second step of the production method (2) can be carried out in the presence of a pyridine compound, a basic compound or both of them, as the case requires. The second step of the production method (2) may be carried out following the first step under such a condition that the pyridine compound used in the first step or the basic compound used as the case requires, still remains. Otherwise, the second step of the production method (2) may be carried out by adding the pyridine compound or the basic compound. The pyridine compound and the basic compound cannot generally be defined due to differences in the raw materials, the type of the solvent or the reaction conditions, but for example, those exemplified in the above-described production method (1) may be mentioned. One or more of them may suitably be selected for use as the pyridine compound or the basic compound. Among such pyridine compounds, preferred may, for example, be an alkyl-substituted pyridine, or pyridine, more preferred may, for example, be methyl- or ethyl-substituted pyridine, or pyridine, further preferred may, for example, be 3-methylpyridine, 2,6-dimethylpyridine or pyridine, and still further preferred may, for example, be 3-methylpyridine or pyridine. Among the basic compounds, preferred may, for example, be a chain or cyclic aliphatic amine, further preferred may, for example, be triethylamine.

The amount of the pyridine compound or the basic compound cannot generally be defined due to differences in the raw materials, the type of the solvent or the reaction conditions, but usually, the amount of each of the pyridine compound and the basic compound, or their total amount, is from 0.1 to 3.5 equivalents, preferably from 0.1 to 3.25 equivalents, to 1 equivalent of the compound of the formula (I).

Further, the pyridine compound or the basic compound may be added and mixed in an optional order. For example, it may be added before and after the addition of the compound of the formula (III), the compound of the formula (IV), the compound of the formula (V) and the solvent, or it may be added simultaneously with any one of them or all of them. Further, the pyridine compound and/or the basic compound may be added in the first step and may be used as it is without additional addition in the second step.

The reaction temperature for the second step of the production method (2) cannot generally be defined due to differences in the raw materials, the type of the solvent or the reaction conditions, and heating or cooling may optionally be carried out. Usually, the reaction is carried out within a range of from 0 to 100° C., preferably from 40 to 80° C.

The reaction time for the second step of the production method (2) cannot generally be defined due to differences in the raw materials, the type of the solvent or the reaction conditions, but usually, it is from one minute to 24 hours, preferably from 30 minutes to 3 hours.

Production Method (3)

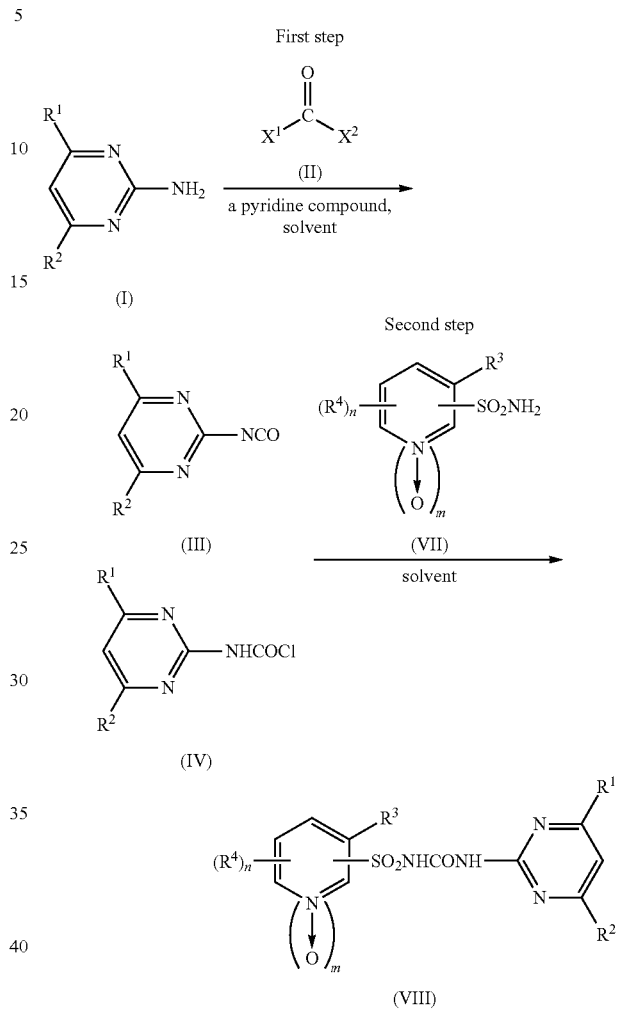

In the above formulae, $R^1$, $R^2$, $R^3$, $R^4$, n and m are as defined above.

The first step of the production method (3) is carried out in accordance with the above-described production method (1).

In the second step of the production method (3), the amount of the compound of the formula (VII) cannot generally be defined due to differences in the raw materials, the type of the solvent or the reaction conditions, but usually, the compound of the formula (VII) is from 0.9 to 3.0 mol, preferably from 0.9 to 1.1 mol, to 1 mol of the compound of the formula (I).

In the second step of the production method (3), the compound of the formula (III) or (IV) and the compound of the formula (VII) may be added and mixed in an optional order. For example, a mixture of the compound of the formula (VII) and the solvent may be preliminarily prepared, and the reaction mixture obtained in the first step may be added thereto without purification, or to the reaction mixture obtained in the first step, the compound of the formula (VII) may be added as it is, or after preliminarily preparing a mixture of the compound of the formula (VII) and the solvent. Preferably, a mixture of the compound of the formula (VII) and the solvent may be preliminarily prepared, and the reaction mixture obtained in the first step may be added thereto without purification.

The second step of the production method (3) can be carried out in the presence of a solvent. The solvent may be any solvent so long as it is inert to the reaction. For example, those exemplified in the production method (1) may be mentioned. One or more of them may suitably be selected for use as the solvent. Among these solvents, preferred may, for example, be a halogenated hydrocarbon or an aromatic hydrocarbon, and more preferred may, for example, be methylene chloride, 1,2-dichloroethane or chlorobenzene.

The amount of the solvent cannot generally be defined due to differences in the raw materials, the type of the solvent or the reaction conditions, but usually, the solvent is from 3 to 35 parts by weight, preferably from 13 to 30 parts by weight, to 1 part by weight of the compound of the formula (I).

The second step of the production method (3) may be carried out in the presence of a pyridine compound, a basic compound or both of them, as the case requires. The second step of the production method (3) may be carried out following the first step under such a condition that the pyridine compound used in the first step or the basic compound used as the case requires, still remains. Otherwise, the second step of the production method (3) may be carried out by adding the pyridine compound or the basic compound. The pyridine compound and the basic compound cannot generally be defined due to differences in the raw materials, the type of the solvent or the reaction conditions, but for example, those exemplified in the above-described production method (1) may be mentioned. One or more of them may suitably be selected for use as the pyridine compound or the basic compound. Among such pyridine compounds, preferred may, for example, be an alkyl-substituted pyridine, or pyridine, more preferred may, for example, be methyl- or ethyl-substituted pyridine, or pyridine, further preferred may, for example, be 3-methylpyridine, 2,6-dimethylpyridine or pyridine, and still further preferred may, for example, be 3-methylpyridine or pyridine, further preferred may be 3-methylpyridine. Among the basic compounds, preferred may, for example, be a chain or cyclic aliphatic amine, more preferred may, for example, be triethylamine.

The amount of the pyridine compound or the basic compound cannot generally be defined due to differences in the raw materials, the type of the solvent or the reaction conditions, but usually, the amount of each of the pyridine compound and the basic compound or their total amount, is from 2.0 to 8.5 equivalents, preferably from 2.0 to 7.5 equivalents, to 1 equivalent of the compound of the formula (I).

Further, the pyridine compound or the basic compound may be added and mixed in an optional order. For example, it may be added before and after the addition of the compound of the formula (III), the compound of the formula (IV), the compound of the formula (VII) and the solvent, or it may be added simultaneously with any one of them or all of them. Further, the pyridine compound and/or the basic compound may be added in the first step and may be used as it is without additional addition in the second step. Preferably, the pyridine compound and/or the basic compound may be added in the first step and used as it is without additional addition in the second step.

The reaction temperature for the second step of the production method (3) cannot generally be defined due to differences in the raw materials, the type of the solvent or the reaction conditions, and heating or cooling may optionally be carried out. Usually, the reaction is carried out within a range of from 0 to 50° C., preferably from 10 to 40° C.

The reaction time for the second step of the production method (3) cannot generally be defined due to differences in the raw materials, the type of the solvent or the reaction conditions, but usually, it is from one minute to 24 hours, preferably from 30 minutes to 3 hours.

Production Method (4)

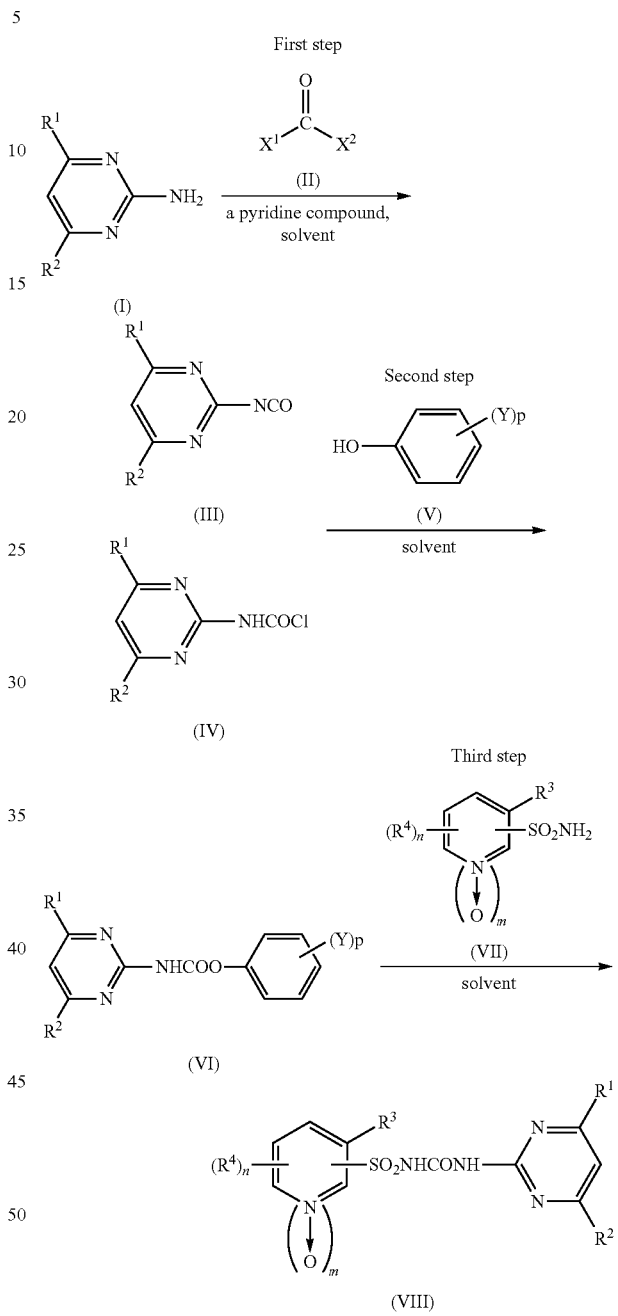

In the above formulae, $R^1$, $R^2$, $R^3$, $R^4$, Y, p, n and m are as defined above.

The first step of the production method (4) is carried out in accordance with the above-described production method (1), and the second step is carried out in accordance with the above-described production method (2).

In the third step of the production method (4), the amount of the compound of the formula (VII) cannot generally be defined due to differences in the raw materials, the type of the solvent or the reaction conditions, but usually, the compound of the formula (VII) is from 0.9 to 3.0 mol, preferably from 0.9 to 1.1 mol, to 1 mol of the compound of the formula (I).

In the third step of the production method (4), the compound of the formula (VI) or (VII) may be added and mixed in an optional order. For example, a mixture of the compound of the formula (VII) and the solvent may be preliminarily prepared, and a mixture of a solvent and the compound of the formula (VI) obtained by liquid-separation operation from the reaction mixture obtained in the second step may be added thereto, or to a mixture of a solvent and the compound of the formula (VI) obtained by liquid separation operation from the reaction mixture obtained in the second step, the compound of the formula (VII) may be added as it is, or after preliminarily preparing a mixture of the compound of the formula (VII) and a solvent. Preferably, to a mixture of a solvent and the compound of the formula (VI) obtained by liquid separation operation from the reaction mixture obtained in the second step, the compound of the formula (VII) may be added without being mixed with a solvent.

The third step of the production method (4) may be carried out in the presence of a solvent. The solvent may be any solvent so long as it is inert to the reaction. For example, those exemplified in the above production method (1) may be mentioned. One or more of them may suitably be selected for use as the solvent. Among these solvents, preferred may, for example, be a halogenated hydrocarbon or an aromatic hydrocarbon, and more preferred may, for example, be methylene chloride, 1,2-dichloroethane or chlorobenzene.

The amount of the solvent cannot generally be defined due to differences in the raw materials, the type of the solvent or the reaction conditions, but usually, the solvent is from 3 to 30 parts by weight, preferably from 10 to 25 parts by weight, to 1 part by weight of the compound of the formula (I).

The third step of the production method (4) may be carried out in the presence of a pyridine compound, a basic compound or both of them, as the case requires. The third step of the production method (4) may be carried out following the first or second step under such a condition that the pyridine compound used in the first or second step or the basic compound used as the case requires, still remains. Otherwise, the third step of the production method (4) may be carried out by adding the pyridine compound or the basic compound. The pyridine compound and the basic compound cannot generally be defined due to differences in the raw materials, the type of the solvent or the reaction conditions, but for example, those exemplified in the above-described production method (1) may be mentioned. One or more of them may suitably be selected for use as the pyridine compound or the basic compound. Among them, preferred may, for example, be an alkali metal carbonate or DBU, further preferred may, for example, be potassium carbonate or DBU, further preferred may, for example, be potassium carbonate. Further, in a case where the basic compound is solid at room temperature, it may be pulverized and used as fine powder, as the case requires, whereby the reactivity may be improved, and the yield may be improved, such being further preferred.

The amount of the pyridine compound or the basic compound to be used cannot generally be defined due to differences in the raw materials, the type of the solvent or the reaction conditions, but usually, the amount of each of the pyridine compound and the basic compound, or their total amount, is from 0.5 to 4.0 equivalents, preferably from 1.0 to 2.2 equivalents, to 1 equivalent of the compound of the formula (I).

Further, the pyridine compound or the basic compound may be added and mixed in an optional order. For example, it may be added before and after the addition of the compound of the formula (VI), the compound of the formula (VII) and the solvent, or it may be added simultaneously with any one of them or all of them. Further, the pyridine compound or the basic compound may be added in the first step and may be used in the second or third step without additional addition.

The reaction temperature for the third step of the production method (4) cannot generally be defined due to differences in the raw materials, the type of the solvent or the reaction conditions, and heating or cooling may optionally be carried out. Usually, the reaction can be carried out within a range of from 0 to 100° C., preferably from 40 to 80° C.

The reaction time for the third step of the production method (4) cannot generally be defined due to differences in the raw materials, the type of the solvent or the reaction conditions, but usually, it is from one minute to 24 hours, preferably from 30 minutes to 3 hours.

Now, preferred embodiments of the present invention will be described, but it should be understood that the present invention is by no means limited thereto.

(a) A method of the above production method (1) wherein the compound of the formula (II) is preliminarily mixed with methylene chloride, 1,2-dichloroethane or chlorobenzene; the compound of the formula (I) is added alone or together with methylene chloride, 1,2-dichloroethane or chlorobenzene, thereto; and then 3-methylpyridine and triethylamine are added, to produce the compound of the formula (III), the compound of the formula (IV) or their mixture.

(b) A method of the above production method (3) wherein the compound of the formula (II) is preliminarily mixed with methylene chloride, 1,2-dichloroethane or chlorobenzene; the compound of the formula (I) is added alone or together with methylene chloride, 1,2-dichloroethane or chlorobenzene, thereto; then 3-methylpyridine and triethylamine are added to produce a reaction mixture containing the compound of the formula (III), the compound of the formula (IV) or their mixture; such a reaction mixture is added to a mixture of the compound of the formula (VII) and methylene chloride, 1,2-dichloroethane or chlorobenzene, preliminarily prepared, to produce the compound of the formula (VIII).

(c) A method for producing the compound of the formula (VIII), which comprises reacting the compound of the formula (VI) with the compound of the formula (VII).

(d) A method of the above production method (1), wherein the reaction of the compound of the formula (I) with the compound of the formula (II) is carried out in the presence of a pyridine compound and a basic compound.

(e) A method of the above production method (2), wherein the reaction of the compound of the formula (I) with the compound of the formula (II), and the reaction of the compound of the formula (III), the compound of the formula (IV) or their mixture, with the compound of the formula (V), are carried out in the presence of a pyridine compound and a basic compound.

(f) A method of the above production method (3), wherein the reaction of the compound of the formula (I) with the compound of the formula (II), and the reaction of the compound of the formula (III), the compound of the formula (IV) or their mixture, with the compound of the formula (VII), are carried out in the presence of a pyridine compound and a basic compound.

(g) A method of the above production method (d), (e) or (f), wherein the pyridine compound is an alkyl-substituted pyridine, or pyridine, and the basic compound is a chain or cyclic aliphatic amine.

(h) A method of the above production method (d), (e) or (f), wherein the pyridine compound is 3-methylpyridine, and the basic compound is triethylamine.

(i) A method of the above production method (4), wherein the reaction of the compound of the formula (I) with the compound of the formula (II), and the reaction of the compound of the formula (III), the compound of the formula (IV) or their mixture, with the compound of the formula (V), are carried out in the presence of a pyridine compound and a basic compound, and the reaction of the compound of the formula (VI) with the compound of the formula (VII) is carried out in the presence of a basic compound.

(j) A method of the above production method (i), wherein the pyridine compound used for the reaction of the compound of the formula (I) with the compound of the formula (II), and for the reaction of the compound of the formula (III), the compound of the formula (IV) or their mixture, with the compound of the formula (V), is an alkyl-substituted pyridine, or pyridine, and the basic compound used for such reactions is a chain or cyclic aliphatic amine, and the basic compound used for the reaction of the compound of the formula (VI) with the compound of the formula (VII) is potassium carbonate.

(k) A method of the above production method (c), wherein the reaction of the compound of the formula (VI) with the compound of the formula (VII) is carried out in the presence of the basic compound.

(l) A method of the above production method (k), wherein the basic compound is potassium carbonate.

(m) A method of the above production method (1), wherein the compound of the formula (I) is reacted with the compound of the formula (II) in the presence of a pyridine compound to produce the compound of the formula (III).

(n) A method of the above production method (2), wherein the compound of the formula (III) produced by reacting the compound of the formula (I) with the compound of the formula (II) in the presence of a pyridine compound, is reacted with the compound of the formula (V) to produce the compound of the formula (VI).

(o) A method of the above production method (3), wherein the compound of the formula (III) produced by reacting the compound of the formula (I) with the compound of the formula (II) in the presence of a pyridine compound, is reacted with the compound of the formula (VII) to produce the compound of the formula (VIII).

(p) A method of the above production method (4), wherein the compound of the formula (III) produced by reacting the compound of the formula (I) with the compound of the formula (II) in the presence of a pyridine compound, is reacted with the compound of the formula (V) to produce the compound of the formula (VI), and the compound of the formula (VI) is reacted with the compound of the formula (VII) to produce the compound of the formula (VIII).

(q) A method of the above production method (1), (2), (3), (4) or (c), wherein $R^1$ and $R^2$ are methoxy simultaneously.

(r) A method of the above production method (3), (4) or (c), wherein $R^1$ and $R^2$ are methoxy simultaneously, $R^3$ is dimethylaminocarbonyl or trifluoromethyl, and each of n and m is 0.

EXAMPLES

Now, Examples of the present invention will be described, but it should be understood that the present invention is by no means thereby restricted.

Now, Examples of the production methods will be described.

Here, $^1$H-NMR is the nuclear magnetic resonance spectroscopy of proton, and the measured data of the chemical shift δ used for identification of compounds will be given. Measurements were carried out by using deuterated chloroform ($CDCl_3$) as a solvent.

Further, GC/MS means gas chromatography/mass spectrometry; m/z means mass/charge number; EI means an electron ionization method; LC/MS means liquid chromatography/mass spectrometry; FAB means fast atom bombardment; and the respective measured data used for identification of compounds will be given.

Example 1

(1) Into a four-necked flask (hereinafter reactor A), 410 g of a preliminarily prepared 14.4 wt % carbonyl chloride/1,2-dichloroethane solution and 1,050 g of 1,2-dichloroethane were introduced, and further, 63.7 g of 2-amino-4,6-dimethoxypyrimidine (purity: 97.3%) was introduced with stirring. Thereafter, a mixed solution of 182 g of triethylamine and 74 g of 3-methylpyridine was dropwise added over a period of 15 minutes. After completion of the dropwise addition, stirring was continued at room temperature for 30 minutes to obtain a reaction mixture containing 4,6-dimethoxypyrimidin-2-ylisocyanate and 4,6-dimethoxypyrimidin-2-ylcarbamoyl chloride. Confirmation of the formation was carried out by sampling a few droplets of the reaction liquid from the reaction mixture, introducing the droplets into about 1 mL of anhydrous methanol for methylcarbamate-conversion, followed by analysis by liquid chromatography to confirm that methyl N-(4,6-dimethoxypyrimidin-2-yl)carbamate was obtained.

(2) Into a separate four-necked flask (hereinafter reactor B), 90.6 g of 2-aminosulfonyl-N,N-dimethylnicotinamide (purity: 96.0%) and 300 g of 1,2-dichloroethane were introduced, and the reaction mixture obtained in the above step (1) was fed by a pump from the reactor A to the reactor B with stirring. After feeding, the reactor A was washed with 100 g of 1,2-dichloroethane, and this washing liquid was also fed to the reactor B. Thereafter, stirring was continued at room temperature for 30 minutes. The reaction mixture was put into a four-necked flask provided with a discharge cock in the bottom and extracted with water. Of the obtained aqueous layer and the organic layer, the organic layer was washed with concentrated sulfuric acid and then washed with water. These washing liquids were put together, and the above aqueous layer was added thereto with stirring to precipitate a solid. The obtained solid was subjected to filtration by a Buchner funnel and washed twice with water. The obtained solid was dried in a hot air dryer to obtain 133.4 g of 2-(4,6-dimethoxypyrimidin-2-ylcarbamoyl sulfamoyl)-N,N-dimethylnicotinamide. The crude yield thereof was 81% based 2-amino-4,6-dimethoxypyrimidine.

Example 2

(1) Into a four-necked flask, 704.88 g of a preliminarily prepared 4.3 wt % carbonyl chloride/methylene chloride solution and 51.15 g of methylene chloride were introduced, and further, 31.00 g of 2-amino-4,6-dimethoxypyrimidine was introduced with stirring at 20° C. under cooling with water. Thereafter, a mixed solution of 90.9 g of triethylamine and 1.86 g of 3-methylpyridine was dropwise added over a period of 30 minutes while maintaining the temperature to be at most 30° C. After completion of the dropwise addition, stirring was continued at room temperature for 2 hours to obtain a reaction mixture containing 4,6-dimethoxypyrimidin-2-ylisocyanate and 4,6-dimethoxypyrimidin-2-ylcarbamoyl chloride. Confirmation of the formation was carried out in the same manner as in the above Example 1.

(2) In a separate four-necked flask, 43.95 g of 2-aminosulfonyl-N,N-dimethylnicotinamide and 145.03 g of methylene chloride were introduced, and the reaction mixture obtained in the above step (1) was dropwise added thereto with stirring at a temperature of at most 30° C. After completion of the dropwise addition, the reaction was carried out at room temperature for one hour. Water was introduced into the reaction mixture, followed by stirring, and the mixture was left to stand still, whereupon the upper aqueous layer was obtained by liquid separation. To the aqueous layer, sulfuric acid (an aqueous solution) was added to adjust the pH to from 3 to 4. The formed slurry was subjected to filtration by a Buchner funnel to obtain crystals. The crystals were washed with water and dried under reduced pressure to obtain 68.88 g of 2-(4,6-dimethoxypyrimidin-2-ylcarbamoyl sulfamoyl)-N,N-dimethylnicotinamide. The crude yield thereof was 84% based on 2-amino-4,6-dimethoxypyrimidine.

Example 3

(1) Into a four-necked flask, 175 g of 1,2-dichloroethane and 7.4 g of trichloromethyl chloroformate were introduced, and 7.78 g of 2-amino-4,6-dimethoxypyrimidine was introduced thereto. Thereafter, a mixed solution of 15.2 g of triethylamine and 0.46 g of 3-methylpyridine was dropwise added while maintaining the temperature to be at most 20° C. under cooling with ice. After completion of the dropwise addition, stirring was carried out at room temperature for 30 minutes to obtain a reaction mixture containing 4,6-dimethoxypyrimidin-2-ylisocyanate and 4,6-dimethoxypyrimidin-2-ylcarbamoyl chloride.

(2) To the reaction mixture obtained in the above step (1), 4.94 g of phenol was introduced, followed by a reaction at 50° C. for one hour. To the reaction solution, dilute hydrochloric acid (an aqueous solution) was added, followed by stirring, and the mixture was left to stand still, whereupon the upper aqueous layer was removed by liquid separation. The obtained 1,2-dichloroethane solution was dehydrated by anhydrous sodium sulfate, and then, anhydrous sodium sulfate was removed by filtration. Thereafter, 1,2-dichloroethane was removed from the filtrate under reduced pressure, and the residue was dried to obtain 15.64 g of phenyl N-(4,6-dimethoxypyrimidin-2-yl)carbamate (purity: 83.6%). The yield thereof was 95% based on 2-amino-4,6-dimethoxypyrimidine.

Example 4

(1) Into a four-necked flask, 429 g of a preliminarily prepared 15.1 wt % carbonyl chloride/methylene chloride solution and 554 g of methylene chloride were introduced, and 77.6 g of 2-amino-4,6-dimethoxypyrimidine was introduced under cooling with ice to a temperature of at most 20° C. A mixed solution of 116.4 g of triethylamine and 4.8 g of 3-methylpyridine was introduced by a rotary pump while maintaining the temperature to be at most 20° C. under cooling with ice. After the introduction, stirring was continued at room temperature for 30 minutes to obtain a reaction mixture containing 4,6-dimethoxypyrimidin-2-ylisocyanate and 4,6-dimethoxypyrimidin-2-ylcarbamoyl chloride.

(2) To the reaction mixture obtained in the above step (1), 49.5 g of phenol was introduced, followed by heating and refluxing for one hour. Water was added to the reaction mixture, followed by stirring, and the mixture was left to stand still, and the upper aqueous layer was removed by liquid separation to obtain a methylene chloride solution of phenyl N-(4,6-dimethoxypyrimidin-2-yl)carbamate.

(3) The methylene chloride solution obtained in the above step (2), was introduced into a separate four-necked flask, and 108.9 g of 2-aminosulfonyl-N,N-dimethylnicotinamide and 69.1 g of potassium carbonate as fine powder, were introduced thereto, followed by heating and refluxing for one hour. Thereafter, water was added, followed by stirring, and the mixture was left to stand still. The lower organic layer was removed by liquid separation, and concentrated hydrochloric acid was dropwise added so that the pH of the aqueous layer became at most 3 to precipitate crystals. The precipitated crystals were subjected to filtration, washed with water and then dried to obtain 178.7 g of 2-(4,6-dimethoxypyrimidin-2-ylcarbamoyl sulfamoyl)-N,N-dimethylnicotinamide. The crude yield thereof was 87% based on 2-amino-4,6-dimethoxypyrimidine.

Example 5

(1) Into a four-necked flask, 576.0 g of a preliminarily prepared 5.50 wt % carbonyl chloride/chlorobenzene solution was introduced, cooled to a temperature of at most 30° C., and 31.0 g of 2-amino-4,6-dimethoxypyrimidine was introduced. Thereafter, a mixed solution of 90.9 g of triethylamine and 1.86 g of 3-methylpyridine was dropwise added while maintaining the temperature to be at most 30° C. under cooling with ice water. After completion of the dropwise addition, stirring was continued at room temperature for one hour to obtain a reaction mixture containing 4,6-dimethoxypyrimidin-2-ylisocyanate and 4,6-dimethoxypyrimidin-2-ylcarbamoyl chloride.

(2) Into a separate four-necked flask, 44.5 g of 3-trifluoromethylpyridine 2-sulfonamide (purity: 96.4%) and 178.6 g of chlorobenzene were introduced, and the reaction mixture obtained in the above step (1) was introduced thereto at a temperature of at most 30° C. After the introduction, stirring was continued at room temperature for one hour. Water was introduced into the reaction mixture, and the chlorobenzene layer was removed by liquid separation. To the aqueous layer, sulfuric acid (an aqueous solution) was dropwise added to adjust the pH to from 2.2 to 2.5 thereby to precipitate crystals. The precipitated crystals were collected by filtration and dried to obtain 68.5 g of 1-(4,6-dimethoxypyrimidin-2-yl)-3-[(3-trifluoromethylpyridin-2-yl)sulfonyl]urea. The crude yield thereof was 84% based 2-amino-4,6-dimethoxypyrimidine.

Example 6

(1) Into a four-necked flask, 185 g of methylene chloride and 7.4 g of trichloromethyl chloroformate were introduced, and 7.76 g of 2-amino-4,6-dimethoxypyrimidine was introduced thereto. Thereafter, a mixed solution of 12.7 g of triethylamine and 0.46 g of 3-methylpyridine was dropwise added while maintaining the temperature to be at most 20° C. under cooling with ice. After completion of the dropwise addition, stirring was continued at room temperature for 30 minutes to obtain a reaction mixture containing 4,6-dimethoxypyrimidin-2-ylisocyanate and 4,6-dimethoxypyrimidin-2-ylcarbamoyl chloride.

(2) To the reaction mixture obtained in the above step (1), 7.1 g of phenol was introduced, followed by heating and refluxing for one hour. The reaction mixture was washed with dilute hydrochloric acid (an aqueous solution) and then left to stand still, whereupon the upper aqueous layer was removed by liquid separation, to obtain a methylene chloride solution of phenyl N-(4,6-dimethoxypyrimidin-2-yl)carbamate.

(3) The methylene chloride solution obtained in the above step (2) was introduced into a separate four-necked flask, and 11.5 g of 2-aminosulfonyl-N,N-dimethylnicotinamide and 6.91 g of potassium carbonate as fine powder were introduced thereto, followed by heating and refluxing for one hour. Thereafter, water was added, followed by stirring, and the mixture was left to stand still, and the lower organic layer was removed by liquid separation. To this organic layer, water was added, followed by stirring, and the mixture was left to stand still, whereupon the lower organic layer was again removed by liquid separation. The obtained all aqueous layers were put together, and concentrated hydrochloric acid was dropwise added so that the pH would be at most 3 thereby to precipitate crystals. The precipitated crystals were collected by filtration, washed with water and then dried to obtain 19.3 g of 2-(4,6-dimethoxypyrimidin-2-ylcarbamoyl sulfamoyl)-N,N-dimethylnicotinamide. The crude yield thereof was 94% based on 2-amino-4,6-dimethoxypyrimidine.

Example 7

(1) Into a four-necked flask, 572.2 g of a preliminarily prepared 3.9 wt % carbonyl chloride/methylene chloride solution was introduced and cooled to at most 20° C., and 23.3 g of 2-amino-4,6-dimethoxypyrimidine was introduced. Thereafter, a mixed solution of 68.3 g of triethylamine and 1.4 g of 3-methylpyridine was dropwise added while maintaining the temperature to be at most 20° C. under cooling with ice water. After completion of the dropwise addition, stirring was continued at room temperature for 30 minutes.

(2) The reaction mixture obtained in the above step (1) was subjected to filtration by means of celite to remove insolubles. Thereafter, methylene chloride and triethylamine were distilled off under reduced pressure. Then, distillation under reduced pressure was carried out to obtain 12.8 g of 4,6-dimethoxypyrimidin-2-ylisocyanate (the crude yield was 47% based on 2-amino-4,6-dimethoxypyrimidine).

$^1$H-NMR (400 MHz, CDCl$_3$) δ ppm, 5.85 (s, 1H), 3.90 (s, 6H), GC/MS m/z (EI+)=181

Example 8

(1) Into a four-necked flask, 1336.9 g of a preliminarily prepared 5.5 wt % carbonyl chloride/chlorobenzene solution was introduced and cooled to at most 20° C., and 71.7 g of 2-amino-4,6-dimethoxypyrimidine was introduced. Thereafter, a mixed solution of 209.5 g of triethylamine and 4.3 g of 3-methylpyridine was dropwise added while maintaining the temperature to be at most 20° C. under cooling with ice water. After completion of the dropwise addition, stirring was continued at room temperature for 30 minutes.

(2) The reaction mixture obtained in the above step (1) was subjected to filtration by means of celite to remove insolubles. Then, chlorobenzene and triethylamine were distilled off under reduced pressure. Then, distillation under reduced pressure was carried out to obtain 13.4 g of 4,6-dimethoxypyrimidin-2-ylisocyanate (the crude yield was 16% based on 2-amino-4,6-dimethoxypyrimidine).

$^1$H-NMR (400 MHz, CDCl$_3$) δ ppm, 5.85 (s, 1H), 3.90 (s, 6H), GC/MS m/z (EI+)=181

Example 9

(1) Into a four-necked flask, 161.6 g of a preliminarily prepared 13.8 wt % carbonyl chloride/methylene chloride solution and 410 g of methylene chloride were introduced and cooled to at most 30° C., and 23.3 g of 2-amino-4,6-dimethoxypyrimidine was introduced. Thereafter, a mixed solution of 68.3 g of triethylamine and 1.4 g of 3-methylpyridine was dropwise added while maintaining the temperature to be at most 30° C. under cooling with ice water. After completion of the dropwise addition, stirring was continued at room temperature for two hours.

(2) To the reaction mixture obtained in the above step (1), 5.04 g of methanol was introduced, followed by stirring at room temperature for 30 minutes. To the reaction mixture, dilute hydrochloric acid (an aqueous solution) was added, followed by stirring, and the mixture was left to stand still, whereupon the upper aqueous layer was removed by liquid separation. The obtained organic layer was dried over anhydrous sodium sulfate, and then anhydrous sodium sulfate was removed by filtration. Thereafter, methylene chloride was distilled off under reduced pressure, followed by drying to obtain 36.6 g of methyl N-(4,6-dimethoxypyrimidin-2-yl) carbamate (purity: 85.1%). The yield thereof was 97% based on 2-amino-4,6-dimethoxypyrimidine.

$^1$H-NMR (400 MHz, CDCl$_3$) δ ppm, 7.52 (s, 1H), 5.73 (s, 1H), 3.91 (s, 6H), 3.78 (s, 3H), LC/MS m/z (FAB+)=214

From this, it is evident that in the above step (1), 4,6-dimethoxypyrimidin-2-ylisocyanate was formed.

Example 10

(1) Into a four-necked flask, 258.7 g of a preliminarily prepared 9.2 wt % carbonyl chloride/chlorobenzene solution and 126 g of chlorobenzene were introduced and cooled to at most 30° C., and 23.3 g of 2-amino-4,6-dimethoxypyrimidine was introduced. Thereafter, a mixed solution of 68.3 g of triethylamine and 1.4 g of 3-methylpyridine was dropwise added while maintaining the temperature to be at most 30° C. under cooling with ice water. After completion of the dropwise addition, stirring was continued at room temperature for two hours.

(2) To the reaction mixture obtained in the above step (1), 5.04 g of methanol was introduced, followed by stirring at room temperature for 30 minutes. To the reaction mixture, dilute hydrochloric acid (an aqueous solution) was added, followed by stirring, and the mixture was left to stand still, whereupon the upper aqueous layer was removed by liquid separation. The obtained organic layer was dried over anhydrous sodium sulfate, and then anhydrous sodium sulfate was removed by filtration. Thereafter, chlorobenzene was distilled off under reduced pressure, followed by drying to obtain 37.7 g of methyl N-(4,6-dimethoxypyrimidin-2-yl)carbamate (purity: 84.8%). The yield thereof was 97% based on 2-amino-4,6-dimethoxypyrimidine.

$^1$H-NMR (400 MHz, CDCl$_3$) δ ppm, 7.62 (s, 1H), 5.73 (s, 1H), 3.90 (s, 6H), 3.77 (s, 3H), LC/MS m/z (FAB+)=214

From this, it is evident that in the above step (1), 4,6-dimethoxypyrimidin-2-ylisocyanate was formed.

Example 11

(1) Into a four-necked flask, 572.2 g of a preliminarily prepared 3.9 wt % carbonyl chloride/methylene chloride solution was introduced and cooled to at most 30° C., and 23.3 g of 2-amino-4,6-dimethoxypyrimidine was introduced. Thereafter, a mixed solution of 68.3 g of triethylamine and 1.4 g of 3-methylpyridine was dropwise added while maintaining the temperature to be at most 30° C. under cooling with ice water. After completion of the dropwise addition, stirring was continued at room temperature for two hours.

(2) Into a separate four-necked flask, 32.7 g of 2-aminosulfonyl-N,N-dimethylnicotinamide and 108.8 g of methylene chloride were introduced, and the reaction mixture obtained in the above step (1) was introduced thereto at a temperature of at most 30° C. After the introduction, stirring was continued at room temperature for one hour. To the reaction mixture, water was introduced, and the methylene chloride layer was removed by liquid separation. To the obtained aqueous layer, concentrated hydrochloric acid was dropwise added to acidify the aqueous layer thereby to precipitate crystals.

The precipitated crystals were collected by filtration and dried to obtain 56.5 g of 2-(4,6-dimethoxypyrimidin-2-ylcarbamoyl sulfamoyl)-N,N-dimethylnicotinamide. The crude yield thereof was 91% based on 2-amino-4,6-dimethoxypyrimidine.

$^1$H-NMR (400 MHz, CDCl$_3$) δ ppm, 8.70-8.68 (m, 1H), 7.75-7.73 (m, 1H), 7.57-7.53 (m, 1H), 5.79 (s, 1H), 4.02 (s, 6H), 3.11 (s, 3H), 2.90 (s, 3H), LC/MS m/z (FAB+)=411

Example 12

(1) Into a four-necked flask, 258.7 g of a preliminarily prepared 9.2 wt % carbonyl chloride/chlorobenzene solution and 126 g of chlorobenzene were introduced and cooled to at most 30° C., and 23.3 g of 2-amino-4,6-dimethoxypyrimidine was introduced. Thereafter, a mixed solution of 68.3 g of triethylamine and 1.4 g of 3-methylpyridine was dropwise added while maintaining the temperature to be at most 30° C. under cooling with ice water. After completion of the dropwise addition, stirring was continued at room temperature for one hour.

(2) Into a separate four-necked flask, 32.3 g of 3-trifluoromethylpyridine 2-sulfonamide and 134.2 g of chlorobenzene were introduced, and the reaction mixture obtained in the above step (1) was introduced thereto at a temperature of at most 30° C. After the introduction, stirring was continued at room temperature for one hour. To the reaction mixture, water was introduced, and the chlorobenzene layer was removed by liquid separation. To the obtained aqueous layer, concentrated hydrochloric acid was dropwise added to acidify the aqueous layer thereby to precipitate crystals. The precipitated crystals were collected by filtration and dried to obtain 51.6 g of 1-(4,6-dimethoxypyrimidin-2-yl)-3-[(3-trifluoromethylpyridin-2-yl)sulfonyl]urea. The crude yield thereof was 84% based on 2-amino-4,6-dimethoxypyrimidine.

$^1$H-NMR (400 MHz, CDCl$_3$) δ ppm, 8.79-8.77 (m, 1H), 8.25-8.23 (m, 1H), 7.69-7.64 (m, 1H), 5.81 (s, 1H), 3.99 (s, 6H), LC/MS m/z (FAB+)=408

Example 13

(1) Into a four-necked flask, 419.6 g of a preliminarily prepared 13.8 wt % carbonyl chloride/methylene chloride solution and 406 g of methylene chloride were introduced and cooled to at most 20° C., and 69.9 g of 2-amino-4,6-dimethoxypyrimidine was introduced. Thereafter, a mixed solution of 107.1 g of triethylamine and 4.2 g of 3-methylpyridine was dropwise added while maintaining the temperature to be at most 20° C. under cooling with ice water. After completion of the dropwise addition, stirring was continued at room temperature for 30 minutes.

(2) To the reaction mixture obtained in the above step (1), 44.5 g of phenol was introduced, followed by heating and refluxing for one hour. To the reaction solution, dilute hydrochloric acid (an aqueous solution) was added and stirred, and the mixture was left to stand still, whereupon the upper aqueous layer was removed by liquid separation to obtain a methylene chloride solution of phenyl N-(4,6-dimethoxypyrimidin-2-yl)carbamate. The reaction solution obtained in this step was equally divided into three portions, which were used for the subsequent reactions.

(3) To ⅓ of the reaction solution obtained in the above step (2), dilute hydrochloric acid (an aqueous solution) was added, followed by stirring, and the mixture was left to stand still, whereupon the upper aqueous layer was removed by liquid separation. The obtained organic layer was dried over anhydrous sodium sulfate, and then, the anhydrous sodium sulfate was removed by filtration. Thereafter, methylene chloride was distilled off under reduced pressure, followed by drying to obtain 46.6 g of phenyl N-(4,6-dimethoxypyrimidin-2-yl) carbamate (purity: 84.1%). The yield thereof was 95% based on 2-amino-4,6-dimethoxypyrimidine.

$^1$H-NMR (400 MHz, CDCl$_3$) δ ppm, 7.85 (s, 1H), 7.40-7.36 (m, 2H), 7.25-7.17 (m, 3H), 5.78 (s, 1H), 3.97 (s, 6H), LC/MS m/z (FAB+)=276

(4) To ⅓ of the reaction solution obtained in the above step (2), 32.7 g of 2-aminosulfonyl-N,N-dimethylnicotinamide and 20.7 g of potassium carbonate as fine powder were introduced, followed by heating and refluxing for one hour. To the reaction mixture, water was introduced, and the organic layer was removed by liquid separation. To this organic layer, water was added, followed by stirring, and the mixture was left to stand still, whereupon the organic layer was again removed by liquid separation. The obtained aqueous layers were put together, and concentrated hydrochloric acid was dropwise added to acidify the aqueous layer thereby to precipitate crystals. The precipitated crystals were collected by filtration and dried to obtain 54.1 g of 2-(4,6-dimethoxypyrimidin-2-ylcarbamoyl sulfamoyl)-N,N-dimethylnicotinamide. The crude yield thereof was 88% based on 2-amino-4,6-dimethoxypyrimidine.

$^1$H-NMR (400 MHz, CDCl$_3$) δ ppm, 8.70-8.68 (m, 1H), 7.75-7.75 (m, 1H), 7.57-7.43 (m, 1H), 5.78 (s, 1H), 4.00 (s, 6H), 3.12 (s, 3H), 2.90 (s, 3H), LC/MS m/z (FAB+)=411

(5) To ⅓ of the reaction solution obtained in the above step (2), 32.3 g of 3-trifluoromethylpyridine 2-sulfonamide and 20.7 g of potassium carbonate as fine powder were introduced, followed by heating and refluxing for one hour. To the reaction mixture, water was introduced, and the organic layer was removed by liquid separation. To this organic layer, water was added, followed by stirring, and the mixture was left to stand still, whereupon the organic layer was again removed by liquid separation. The obtained aqueous layers were put together, and concentrated hydrochloric acid was dropwise added to acidify the aqueous layer thereby to precipitate crystals. The precipitated crystals were collected by filtration and dried to obtain 51.2 g of 1-(4,6-dimethoxypyrimidin-2-yl)-3-[(3-trifluoromethylpyridin-2-yl)sulfonyl]urea. The crude yield thereof was 84% based on 2-amino-4,6-dimethoxypyrimidine.

$^1$H-NMR (400 MHz, CDCl$_3$) δ ppm, 8.78 (d, J=4.4 Hz, 1H), 8.24 (d, J=8 Hz, 1H), 7.66 (dd, J=8.0, 4.5 Hz, 1H), 5.81 (s, 1H), 3.99 (s, 1H), LC/MS m/z (FAB+)=408

INDUSTRIAL APPLICABILITY

According to the present invention, it is possible to produce the compound of the formula (III) or (IV) in high yield by a simple operation. And, a sulfonylurea compound such as the compound of the formula (VIII) which is useful as an active ingredient for agricultural chemicals can be produced simply in high yield with little impurities. Therefore, the industrial applicability of the present invention is very high.

The entire disclosure of Japanese Patent Application No. 2008-108898 filed on Apr. 18, 2008 including specification, claims, drawings and abstract is incorporated herein by reference in its entirety.

The invention claimed is:

1. A method which comprises:
reacting a compound represented by the formula (I):

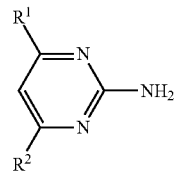

(I)

wherein each of $R^1$ and $R^2$ is methyl, methoxy or ethoxy, and $R^1$ and $R^2$ may be the same or different from each other, with a compound represented by the formula (II):

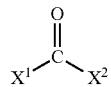

(II)

wherein each of $X^1$ and $X^2$ is a chlorine atom or —$OCCl_3$, and $X^1$ and $X^2$ may be the same or different from each other in the presence of a pyridine compound and a basic compound selected from the group consisting of a chain aliphatic amine and a cyclic aliphatic amine, to produce a compound represented by the formula (III):

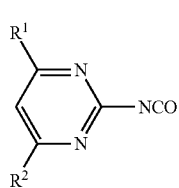

(III)

wherein $R^1$ and $R^2$ are as defined above, a compound represented by the formula (IV):

(IV)

wherein $R^1$ and $R^2$ are as defined above, or their mixture.

2. The method according to claim 1, wherein the pyridine compound is an alkyl-substituted pyridine or pyridine.

3. The method according to claim 1, wherein the pyridine compound is 3-methylpyridine, and the basic compound is triethylamine.

4. The method according to claim 1, wherein the compound of formula (I) is added to the compound of formula (II) during the reacting.

5. The method according to claim 1, wherein the compound of formula (I) is added to the compound of formula (II) to form a mixture, and subsequently the pyridine compound and the basic compound are added to the mixture and the reacting is carried out.

6. The method according to claim 1, wherein the reacting is carried out in a solvent consisting of halogenated compounds.

7. The method according to claim 1, wherein the reacting is carried out at a temperature of from 10 to 40° C.

8. The method according to claim 4, wherein the compound of formula (I) is added to the compound of formula (II) at a temperature of 20-40° C.

9. The method according to claim 4, wherein the compound of formula (II) is phosgene.

10. The method according to claim 9, wherein the pyridine compound is 3-methylpyridine and the basic compound is triethylamine, and wherein the compound of formula (I) is added to the phosgene to form a first mixture at a temperature of 20-40° C., then a second mixture of 3-methylpyridine and triethylamine is added to the reaction mixture and the reacting is carried out.

* * * * *